United States Patent [19]

Rafaeli

[11] Patent Number: 5,190,062
[45] Date of Patent: Mar. 2, 1993

[54] PERSONAL DENTAL FLOSS HOLDER AND METHOD

[76] Inventor: David Rafaeli, 22632 Blue Fin Trail, Boca Raton, Fla. 33428

[21] Appl. No.: 802,317

[22] Filed: Dec. 4, 1991

[51] Int. Cl.⁵ .............................................. A61C 15/00
[52] U.S. Cl. .................................................... 132/323
[58] Field of Search ............... 132/323, 324, 325, 326, 132/327; 128/62 A; 433/6

[56] References Cited

U.S. PATENT DOCUMENTS

| | | | |
|---|---|---|---|
| 2,197,345 | 4/1940 | Meyer | 132/325 |
| 3,335,718 | 8/1967 | Sexton | 128/62 A |
| 3,848,335 | 11/1974 | Bergersen | 433/6 |
| 3,874,084 | 4/1975 | Cole | 128/62 A |
| 4,440,184 | 4/1984 | Smith | 132/323 |
| 4,832,062 | 5/1989 | Grollimund et al. | 132/327 |
| 5,022,417 | 6/1991 | Cimini | 132/323 |

FOREIGN PATENT DOCUMENTS 2923057  12/1980  Fed. Rep. of Germany ...... 132/323

Primary Examiner—John J. Wilson

[57] ABSTRACT

A dental flosser holds a plurality of threads especially spaced for insertion between teeth of a particular user for whom the flosser is custom made.

15 Claims, 2 Drawing Sheets

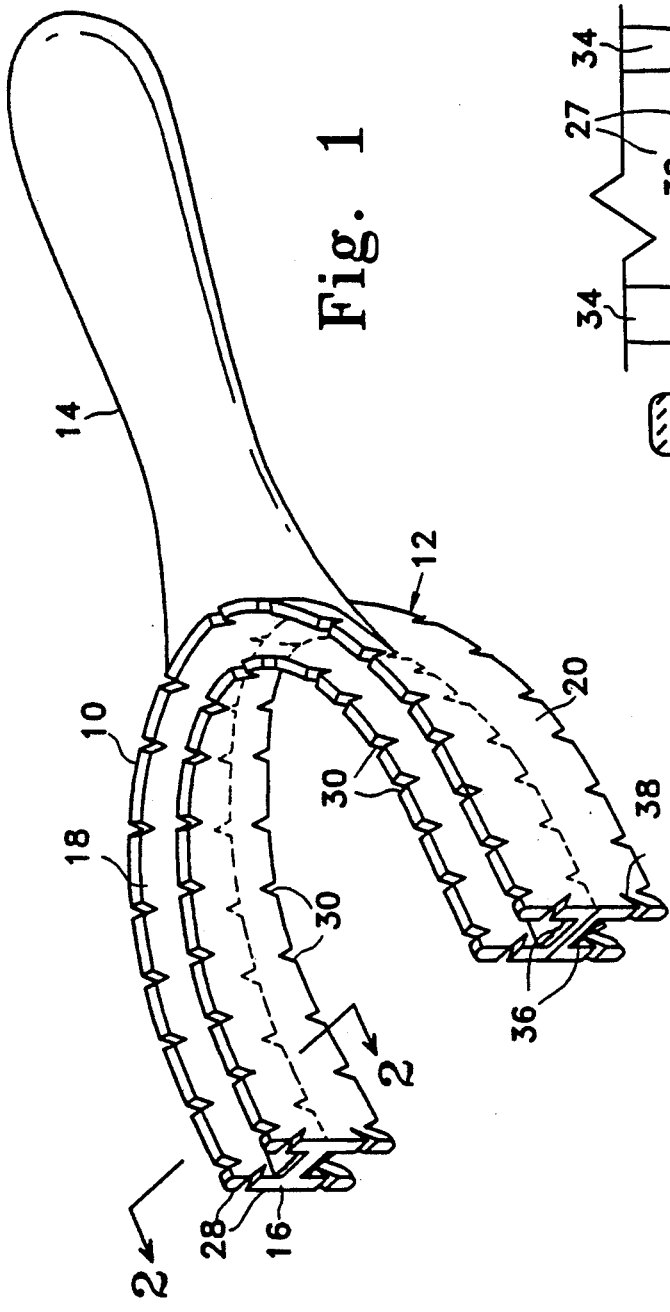
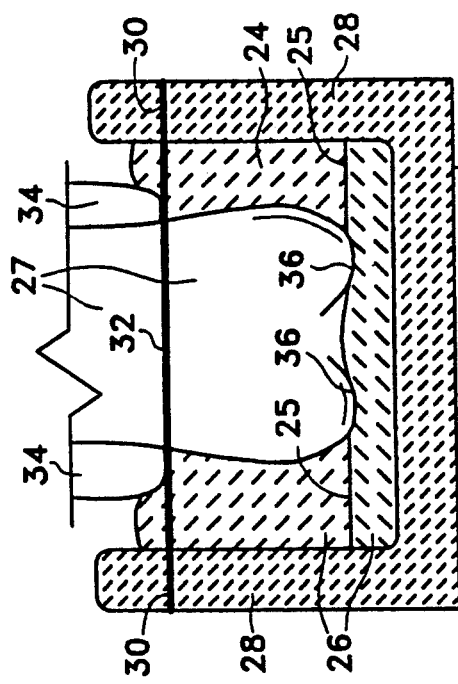
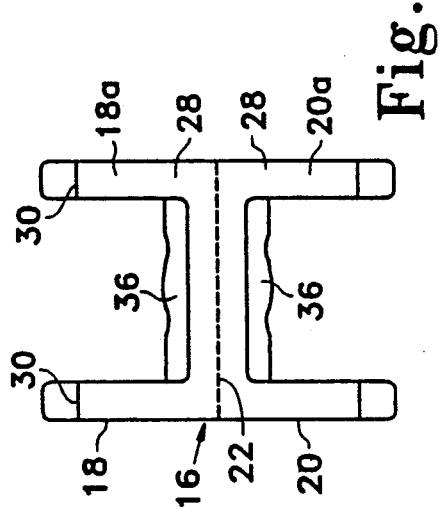

5,190,062

PERSONAL DENTAL FLOSS HOLDER AND METHOD

SUMMARY OF THE INVENTION

This invention relates to a novel dental floss holder customized for use by an individual user. The invention may be adapted to be used to floss all of the user's teeth at one time, or may be provided in one or more sections adapted to floss only specific teeth of the user.

A primary object of this invention is to provide a dental floss holder adapted to position one or more lengths of floss in proper relative relationship between individual teeth of the user for whom the floss holder is customized.

Another primary object of this invention is to provide one, or more, floss holders customized to guide floss between a plurality of selected teeth of the user.

A third object of the invention is to design a floss holder easy to load with floss and which can be easily cleaned and in which the floss can be replaced easily and simply.

A fourth primary object of the invention is to provide impression means to customize the floss holder to fit the floss between the teeth of the intended user.

A fifth primary object of the invention is to provide fastening means to keep the floss in tension when inserted between the user's teeth during flossing.

A sixth object is to provide a floss dispenser.

These objects and advantages, and others, will be illustrated and set forth in the drawings and the detailed description to follow.

DESCRIPTION OF THE DRAWINGS

FIG. 1 is a perspective view of a preferred embodiment of the invention for use on both upper and lower jaws;

FIG. 2 is a section taken along the line 2—2 in FIG. 1;

FIG. 3. is an enlarged sectional portion of a form of the invention similar to the upper portion of FIG. 2, intended for use only on the upper teeth of the user, showing a tooth impressed in the impression material.

Figure 4:
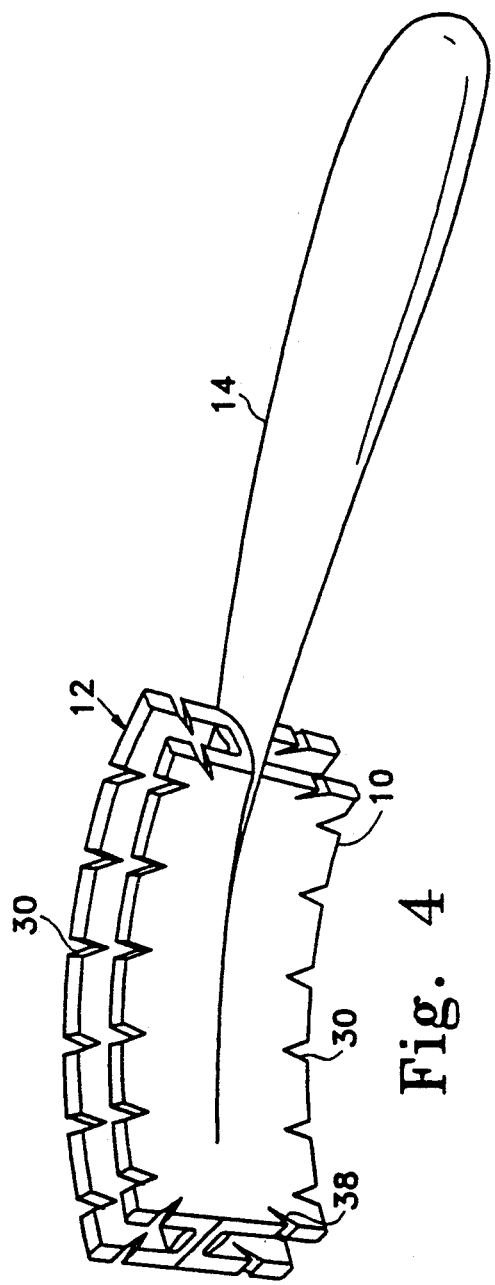
FIG. 4. is a perspective of another form of the invention for use on the upper and lower teeth on the left side of the user's jaw.
Figure 5:
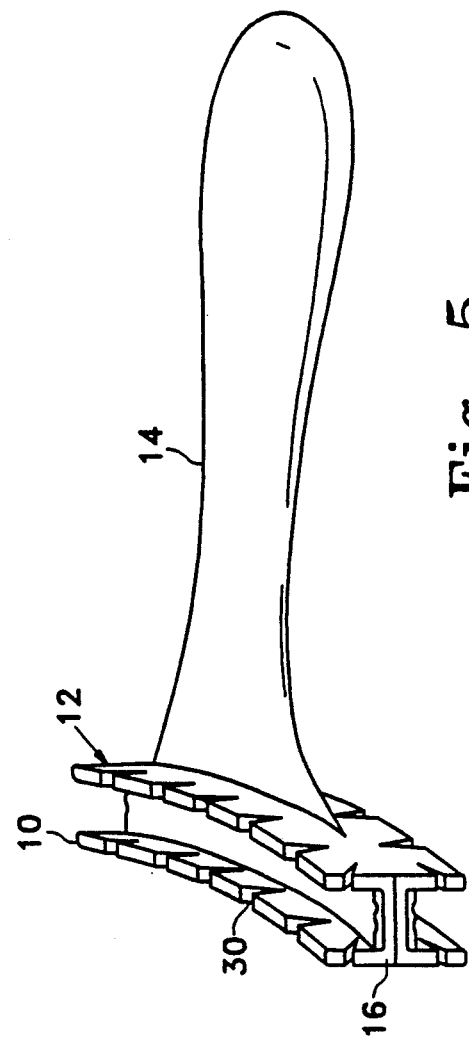
FIG. 5. is a perspective of another form of the invention for use only on the uppers and lowers of the front teeth of the user's jaws.
Figure 6:
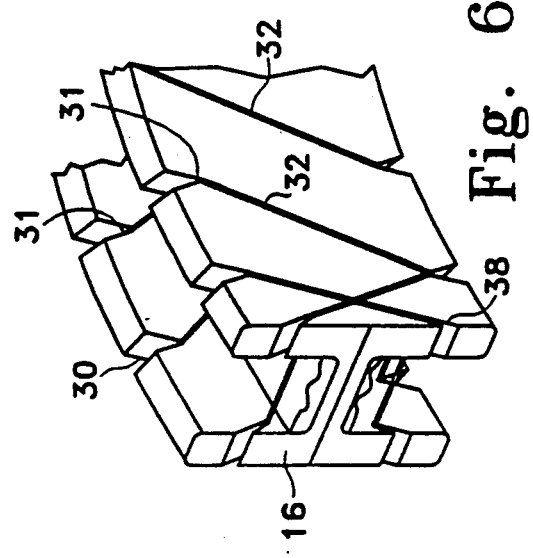
FIG. 6. is a blown up perspective similar to the left ends of FIG. 1 and FIG. 4, including dental floss in position for flossing and floss fastening means.

It is to be understood that these drawings illustrate the invention and that the positionings of the various parts and features may be varied in size and positions to suit the proportions of the teeth, gums and jaws of the user for whom they are customized.

DETAILED DESCRIPTION

Reference to FIG. 1 shows a drawing of a first form of the invention which includes a body portion 10 in the form of a dental floss holder 12 comprising an optional handle 14. The body portion 10 may have an H shaped cross section 16. The upper part 18 of the H shaped cross section 16 comprises a U shaped cross section 18a and the lower part 20 comprises an inverted U shaped cross section 20a. In other forms of the invention the upper parts 18a and the lower parts 20a may be formed seperately for upper and lower teeth of a user as indicated by the dotted line 22 in FIG. 2.

The word "floss" as used herein includes any thread or similar material for floss type tooth cleaning. The term "impression material" as used herein includes material which can be used by the dental profession for making casts.

FIG. 3 is a cross section of a form of the invention for use only on the upper teeth. The bottom 22a defines the lower side of its U shape. The cross sectional construction of this FIG. 3 form is somewhat enlarged to show clearly the method of construction of the invention for all forms and the methods of use and the preferred construction of these forms.

There is at least one layer of impression material 24 to form at least one impression mold area 26 which will be defined by the teeth 27 and gums 34 of the particular individual for whom a form of the invention is crafted. Side walls 28 include floss guides 30 to position the floss 32 properly between the teeth of the person who uses the invention. The flosser 12 is completed for a particular individual by loading the impression mold area 26 with impression material 24 well known in the art. Impression mold materials used in the dental arts may be used. The mold containing the impression material is placed in the user's mouth in the usual manner and the user bites into the impression material, keeping the jaws tight until impression material sets.

After the impression material sets to the desired consistency the next step is to remove the impression from the user's jaw. The next step is to form floss guides 30, preferably V shaped. The floss guides 30, when properly located and cut out, will guide floss 32 between the user's teeth with the apex of the floss guide 30 guiding the floss 32 to the optimal depth (or height) in the flosser 12 to position the floss 32 properly to floss up to and slightly beyond the the gum line without cutting into and injuring the gum 34 of the user. The dental technician can easily determine the proper depth by examining the line where the gum 34 ends in the set impression material 24. This will prevent the floss 32 from positioning too deeply and possibly injuring the gum 34.

The next step is to remove the excess impression material 24 located between opposed floss guides 30 down to a line (indicated by reference numeral 25) leaving impressions 36 of the biting or chewing ends of the teeth 27 in mold area 26.

The floss 32, when loaded into the floss guides 30, may be secured by floss fastening means such as cleat formations 38.

The device, when completed for the intended individual, is used by inserting the desired size and configuration of floss holder 12 at the proper position of the user's mouth for which it is designed.

The user then clenches his, or her, jaws causing the floss 32 loaded in the floss guides 30 to be inserted between the user's teeth. To faciliate the insertion of the floss 32 the user can move the lower jaw from side to side and front to back while clenching the jaws. Holding the handle 14, the user can pull the flosser 12 forward, pressing the floss 32 against the back surfaces of the side teeth and at the same time moving the lower jaw up and down. This will cause the dental floss 32 to scrape the back surfaces of the side teeth. By repeating the same proceedure, except that the user pushes the floss holder 12 backwards, the front surfaces of the side teeth are flossed.

To floss the side surfaces of the front teeth, the user first presses the floss holder 12 to one side (for example, the right side) and moves the lower jaw up and down to floss the left side of the front teeth. Then the user presses the floss holder 12 to the left side to floss the right surfaces of the front teeth.

The above descriptions illustrate the preferred forms of my invention, and I do not wish to be limited by them, but desire to be protected for all forms coming within the claims set forth below.

I claim:

1. A customized dental floss holder for holding dental floss for personal dental use comprising:

a body portion crafted for a particular individual;

adapted to be fitted to a portion of at least one jaw of the individual;

including floss guides positioned to place dental floss at the proper relative position between teeth selected for flossing; and including at least one mold portion of an end of at least one of the mentioned individual's teeth.

2. A dental floss holder according to claim 1 in which the body portion is adapted to be fitted to the jaw of the individual.

3. A dental floss holder according to claim 1 in which a plurality of body portions are adapted to be fitted to a plurality of jaw portions.

4. A dental floss holder according to claim 1 in which the body portion is adapted to be fitted to both jaws of the individual.

5. A dental floss holder according to claim 1 comprising a plurality of floss guides positioned to guide floss between a plurality of a particular user's teeth.

6. A dental floss holder according to claim 1 in which the floss guides are positioned to place the floss between the user's teeth without cutting into the user's gum.

7. A dental floss holder according to claim 1 in which each tooth mold portion has at least one end in alignment with a pair of floss guides.

8. A dental floss holder according to claim 7 including floss fastening means.

9. A method for making a personalized dental floss holder comprising the steps of:

selecting a dental mold holder having at least one U-shaped cross section;

loading the mold holder with impression material;

making an impression of a plurality of a user's teeth;

removing the impression; and making floss guides in the mold holder walls to guide floss between adjoining ends of at least two of the user's mentioned teeth.

10. A method for making a personalized dental floss holder according to claim 9 comprising the further step of:

placing floss guides in positions to guide floss between at least three adjoining teeth of the user.

11. A method according to claim 10 comprising the further step of:

loading the floss guides with floss.

12. A method for using a floss holder according to claim 11 including the steps of:

moving floss between different teeth at different times.

13. A method for using a floss holder according to claim 11 including the step of:

moving the floss holder up and down.

14. A method for using a floss holder according to claim 11 including the steps of:

moving the floss holder in various directions.

15. A method for using a floss holder according to claim 14 including the step of:

movement of the lower jaw of the user.

* * * * *